United States Patent
Willan

(10) Patent No.: US 10,634,593 B2
(45) Date of Patent: Apr. 28, 2020

(54) TESTING METHOD FOR HYDROGEN EMBRITTLEMENT

(71) Applicant: GOFF OMEGA HOLDINGS, LLC, Houston, TX (US)

(72) Inventor: W Craig Willan, Kilauea, HI (US)

(73) Assignee: GOFF OMEGA HOLDINGS, LLC, Fort Worth, TX (US)

(*) Notice: Subject to any disclaimer, the term of this patent is extended or adjusted under 35 U.S.C. 154(b) by 174 days.

(21) Appl. No.: 15/889,438

(22) Filed: Feb. 6, 2018

(65) Prior Publication Data

US 2018/0238783 A1    Aug. 23, 2018

Related U.S. Application Data

(60) Provisional application No. 62/460,147, filed on Feb. 17, 2017.

(51) Int. Cl.
*G01N 3/02* (2006.01)
*G01N 3/18* (2006.01)
(Continued)

(52) U.S. Cl.
CPC .......... *G01N 3/02* (2013.01); *G01N 3/04* (2013.01); *G01N 3/18* (2013.01); *G01N 3/567* (2013.01);
(Continued)

(58) Field of Classification Search
CPC .......... G01N 3/02; G01N 3/18; G01N 3/567; G01N 3/04; G01N 2203/0003;
(Continued)

(56) References Cited

U.S. PATENT DOCUMENTS

| 3,455,152 A | 7/1969 | Maker |
| 3,572,102 A * | 3/1971 | Baratta .................. G01N 3/08 73/856 |

(Continued)

FOREIGN PATENT DOCUMENTS

| CN | 102455342 A | 5/2012 |
| JP | 2009-069004 A | 4/2009 |

(Continued)

OTHER PUBLICATIONS

Ogata, T. "Hydrogen Embrittlement Evaluation in Tensile Properties of Stainless Steels at Cryogenic Temperatures". AIP Conference Proceedings, 986, 12 (2008) (Year: 2008).*

(Continued)

*Primary Examiner* — Jonathan M Dunlap
(74) *Attorney, Agent, or Firm* — Bracewell LLP; James E. Bradley; Kevin R. Tamm

(57) ABSTRACT

A method for testing for hydrogen embrittlement, including mounting a container around a steel alloy test specimen, the container having a closed bottom below a notched area on the test specimen and an open upper end above the notched area; applying a tensile load to the test specimen and sustaining the load for a selected duration to incubate potential hydrogen embrittlement cracks with a sub-critical flaw size if sufficient hydrogen in dangerous levels is present in the test specimen; then, while sustaining the load, dispensing a cryogenic fluid into the container, immersing and chilling the notched area, reducing the sub-critical flaw size for any hydrogen embrittlement cracks incubated; and with the sustained load, fracturing the notched area if the sub-critical flaw size of any hydrogen embrittlement cracks incubated reaches a critical flaw size.

19 Claims, 1 Drawing Sheet

(51) Int. Cl.
G01N 3/04 (2006.01)
G01N 3/56 (2006.01)
(52) U.S. Cl.
CPC ............ G01N 2203/0003 (2013.01); G01N 2203/0017 (2013.01); G01N 2203/027 (2013.01); G01N 2203/0228 (2013.01)
(58) Field of Classification Search
CPC ..... G01N 2203/0017; G01N 2203/027; G01N 2203/0228
See application file for complete search history.

(56) References Cited

U.S. PATENT DOCUMENTS

| | | | |
|---|---|---|---|
| 4,064,438 A | 12/1977 | Alex et al. | |
| 4,221,651 A | 9/1980 | Mansfeld et al. | |
| 4,461,168 A * | 7/1984 | Kobayashi | G01N 3/20 73/851 |
| 4,715,218 A | 12/1987 | Sato et al. | |
| 5,505,095 A * | 4/1996 | Raymond | G01N 3/04 73/831 |
| 5,549,007 A * | 8/1996 | Raymond | G01N 3/04 73/831 |
| 5,585,570 A * | 12/1996 | Raymond | G01N 3/04 73/799 |
| 7,089,802 B2 * | 8/2006 | Tran | G01N 3/20 73/849 |
| 7,852,554 B2 * | 12/2010 | Le Gros | G02B 21/33 359/391 |
| 7,967,927 B2 | 6/2011 | Kuehmann et al. | |
| 9,151,706 B2 | 10/2015 | Wada | |
| 9,176,039 B2 * | 11/2015 | Tran | G01N 3/20 |
| 2002/0167988 A1 * | 11/2002 | Zhu | G01N 25/16 374/55 |
| 2004/0060620 A1 | 4/2004 | Ma et al. | |
| 2005/0050961 A1 * | 3/2005 | Tran | G01N 3/20 73/799 |
| 2010/0070203 A1 * | 3/2010 | Tognarelli | G01N 3/18 702/35 |
| 2014/0238145 A1 * | 8/2014 | Tran | G01N 3/20 73/851 |
| 2014/0352451 A1 * | 12/2014 | Kismarton | G01N 3/02 73/826 |
| 2015/0337408 A1 | 11/2015 | Schulz et al. | |

FOREIGN PATENT DOCUMENTS

| | | |
|---|---|---|
| JP | 2015-052478 A | 3/2015 |
| JP | 2016121947 A | 7/2016 |
| KR | 10-2016-0077326 A | 7/2016 |

OTHER PUBLICATIONS

Kim et al. "Elasto-Visco-Plastic-Damage Model for Pre-Strained 304L Stainless Steel subjected to Low Temperature". World Academy of Science, Engineering and Technology International Journal of Mechanical and Mechatronics Engineering vol. 6, No. 1, 2012 (Year: 2012).*

Mosborg, R.J. "Apparatus for Low-Temperature Tensions Tests of Metals". Engineering Studies Structural Research Series No. 23. (Year: 1951).*

L. Vergani, Hydrogen Effect on Fatigue Behavior of a Quenched and Tempered Steel, Science Direct, Procedia Engineering 74, 468-471, Jun. 29, 2014.

T. Michler, Hydrogen Environment Embrittlement Testing at Low Temperatures and High Pressures, Corrosion Science 50, 3519-3526, Sep. 25, 2008.

International Search Report and Written Opinion dated Aug. 23, 2018 for corresponding PCT/US2018/017008.

* cited by examiner

TESTING METHOD FOR HYDROGEN EMBRITTLEMENT

PRIORITY

This non-provisional patent application claims priority to and the benefit of U.S. Prov. App. Ser. No. 62/460,147, filed Feb. 17, 2017, the entire disclosure of which is incorporated here by reference.

BACKGROUND

Field

The present disclosure relates to methods and systems for testing steel specimens for hydrogen embrittlement, and in particular to incubating micro-cracks by applying a tensile load to a test specimen for a selected time period, then while sustaining the load, chilling the test specimen with liquid nitrogen and/or other cryogenic fluid.

Description of Related Art

The presence of hydrogen within steel and steel alloys causes embrittlement or the potential for weakening and failure of the steel and steel alloys under stress. Hydrogen embrittlement testing is important to industries, such as for example the airline industry, where steel must be tested for structural integrity. Current systems and methods for hydrogen embrittlement testing require extensive periods of time, for example about 200 hours or greater.

SUMMARY

Disclosed here are systems and methods for hydrogen embrittlement testing of metal samples, for example stainless steel and related alloys, which allow for greatly reduced time periods required for testing a metal sample, for example about 20 hours or about 1/10 the time presently required to test for hydrogen embrittlement in metal samples. By applying cryogenic temperatures to a metal sample, accurate, efficient, and consistent testing for hydrogen embrittlement is shown. The surprising and unexpected results shown here provide advantageous systems and methods for testing metal samples in a wide array of industries and applications.

In one embodiment, a method for testing for hydrogen embrittlement is disclosed including the steps of applying a tensile load to a metal test specimen comprising a notched area and sustaining the load for a selected duration to incubate potential hydrogen embrittlement cracks with a sub-critical flaw size if sufficient hydrogen is present in the test specimen; then, while sustaining the load, immersing and chilling the notched area with a cryogenic fluid reducing the sub-critical flaw size for any hydrogen embrittlement cracks incubated; and with the sustained load, fracturing the notched area if the sub-critical flaw size of any hydrogen embrittlement cracks incubated reaches a critical flaw size.

In some embodiments, the step of immersing and chilling the notched area with a cryogenic fluid is carried out using a cryogenic assembly disposed around the metal test specimen. In certain embodiments, the cryogenic assembly comprises a container having a closed bottom below the notched area on the test specimen and an open upper end above the notched area. Still in other embodiments, the step of immersing and chilling the notched area includes dispensing a cryogenic fluid comprising liquid nitrogen and comprises continuing to dispense the cryogenic fluid until rapid boiling of the cryogenic fluid ceases around the metal test specimen. In some embodiments, the step of immersing and chilling the notched area comprises continuing to dispense the cryogenic fluid until the notched area reaches a temperature of the cryogenic fluid.

Still in other embodiments of the method, if any fracturing of the notched area occurs, it will occur within a few seconds to a few minutes after chilling the notched area. In certain embodiments, the step of applying the tensile load for a selected duration occurs while the test specimen is at room temperature. In other embodiments, the step of applying the tensile load for a selected duration occurs while the test specimen is at an elevated temperature above room temperature; and the selected duration while at the elevated temperature is less than the selected duration while at room temperature.

Other embodiments of the method further include the step of applying a castable metallic masking to at least a portion of the metal test specimen. In some embodiments, the selected duration is determined by comparing the time it takes to fracture at room temperature test specimens having known hydrogen at dangerous levels versus a time it takes to fracture identically prepared test specimens having known hydrogen at dangerous levels when chilled with liquid nitrogen. Still in yet other embodiments, the cryogenic fluid comprises a cryogenic fluid other than liquid nitrogen. In some embodiments, the cryogenic fluid comprises a combination of a light aromatic hydrocarbon, such as for example benzyl alcohol, and dry ice ($CO_2$).

Additionally disclosed here is a system for testing for hydrogen embrittlement, the system comprising: a securing mechanism for securing a metal sample; a tension applying mechanism for applying tension to the metal sample once secured by the securing mechanism; and a cryogenic assembly for applying a cryogenic fluid to the metal sample under atmospheric pressure to test for hydrogen embrittlement of the metal sample while the metal sample is under tension. In some embodiments of the system, the cryogenic fluid comprises liquid nitrogen, and the tension applied to the metal sample is between about 5,000 pounds to about 15,000 pounds. In other embodiments, the cryogenic assembly comprises an open-top cup assembly operable to allow for pouring of liquid nitrogen to surround the metal sample while the metal sample is under tension.

In certain embodiments, the securing mechanism and tension applying mechanism comprise threads. In other embodiments, included is a heating mechanism operable to heat the metal sample during tension and prior to applying the cryogenic fluid. Still other embodiments of the system include a sealing mechanism between the tension applying mechanism, the cryogenic assembly, and the metal sample operable to prevent leakage of the cryogenic fluid from the cryogenic assembly. In some embodiments, the system is operable to test more than one metal sample simultaneously for hydrogen embrittlement. And in some embodiments, a temperature measuring mechanism is included to detect when the temperature of the metal sample is at about the temperature of the cryogenic fluid.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

DETAILED DESCRIPTION

Figure 1A:
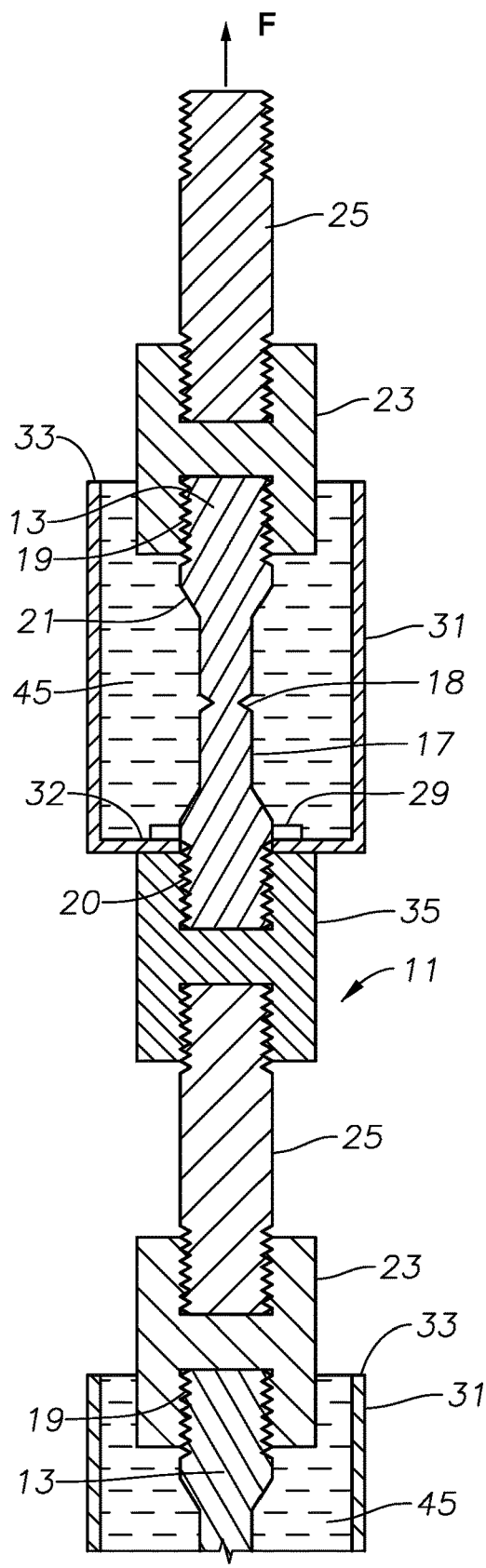
FIGS. 1A and 1B comprise a sectional view of two test specimens being tested for hydrogen embrittlement in accordance with this disclosure.

The methods and systems of the present disclosure will now be described more fully hereinafter with reference to the accompanying drawings in which example embodiments are shown. The methods and systems of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes +/−5% of the cited magnitude. In an embodiment, usage of the term "substantially" includes +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Figure 1B:
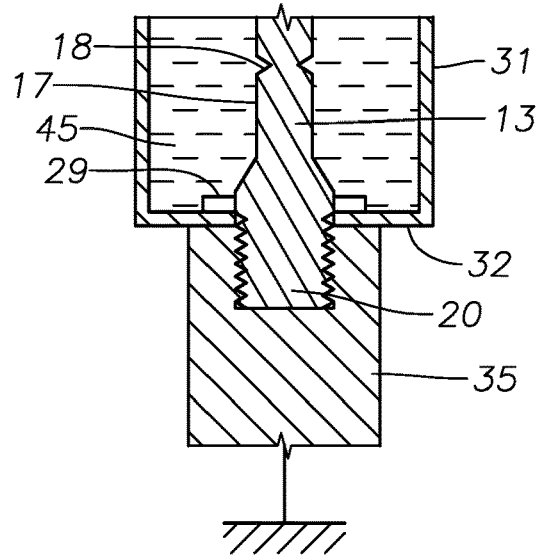

Referring to FIGS. 1A and 1B, a test assembly 11 is employed for hydrogen embrittlement testing in accordance with this disclosure. Hydrogen embrittlement is a phenomena occurring in many high strength metals such as steel alloys. The presence of atomic or molecular hydrogen within the metallurgical structure of the metal can cause the metal to fail under load at a stress significantly lower than predicted or expected. Hydrogen embrittlement can be caused, for example, by a plating or metal finishing process. The consequences of early failure can be catastrophic, if for example, the hydrogen embrittlement failure subsequently occurs in a critical aircraft part. In the past, tests for hydrogen embrittlement generally have involved applying a sustained tensile load on a test specimen at room temperature over a fairly lengthy period of time, such as about 200 hours.

In this disclosure, test assembly 11 has upper and lower test specimens 13. In other embodiments, one of the test specimens 13 could be eliminated or more than test specimen 13 could be included in test assembly 11. Test specimens 13 are identical, each comprising a cylindrical rod or bar formed of the metal, for example steel alloy, to be tested. In this example, each test specimen 13 has a cylindrical downturned area 17 with a notch 18 formed halfway along the length of downturned area 17. Notch 18 extends circumferentially completely around downturned area 17 and is V-shaped in cross-section. The length of downturned area 17 is much longer than the axial dimension of notch 18. Upper and lower externally threaded ends 19, 20 are located at the upper and lower ends of each test specimen 13. Chamfers or bevels 21 join downturned area 17 to upper and lower threaded ends 19, 20. As an example, the outer diameter of threaded ends 19, 20 may be 0.375 inch, the outer diameter of downturned area 17 may be 0.25 inch, and the diameter of notch 18 may be 0.175 inch, but those dimensions can differ.

Various arrangements may be employed to place test specimens 13 in tension. In this example, upper threaded end 19 secures to an upper female connector 23, which may have polygonal flats on its exterior to tighten it. Connector 23 secures to a rod 25 having upper and lower threaded ends. Rod 25 has a larger diameter than downturned area 17. The upper end of rod 25 secures to a part of test assembly 11 that leads to a source (not shown) for applying and sustaining an upward tensile force F.

A thin washer or nut 29, which may be of stainless steel, engages the threads on the upper portion of lower threaded end 20. Nut 29 is thus located on each test specimen 13 at the junction of the lower threaded end 20 and the lower bevel 21. Nut 29 has polygonal drive flats on the exterior to receive a wrench for tightening. Nut 29 is axially very thin, such as having a thickness of only about 0.025 inch.

A container or cup assembly 31 has a hole its bottom 32 to enable cup assembly 31 to slide up over the lower threaded end 20 of one of the test specimens 13. The inside of cup assembly 31, for example upper side of bottom 32, will abut the lower side of nut 29, which has a cross-sectional area greater than the hole in bottom 32. Cup assembly 31 is a cylindrical receptacle with an open upper end 33 that is located above downturned area 17, and in this instance surrounds a lower part of connector 23. Cup assembly 31 may be formed of various materials, such as plastic, aluminum, or stainless steel. Cup assembly 31 has an inner diameter greater than the outer diameter of connector 23 so as to provide fluid (liquid and/or gas) input access to open upper end 33. Cup assembly 31 has very thin walls to reduce the mass of cup assembly 31.

A lower female connector 35 secures to the threads on test specimen lower threaded end 20. The upper end of lower female connector 35 abuts the lower side of cup bottom 32. Tightening lower female connector 35 squeezes cup bottom 32 between nut 29 and lower female connector 35 to form a seal around the hole in cup bottom 32. In some embodiments, an adhesive, sealant, and/or gasket may be added to the interface between nut 29, lower female connector 35, and cup bottom 32 to prevent cryogenic fluid from leaking out of cup assembly 31.

In other embodiments, other types and configurations of cryogenic assemblies could be used. For example, a closed-top cryogenic assembly could be used, in which one or more cryogenic fluid injection ports existed at one or more points disposed within a sidewall, top, and/or bottom of the cryogenic assembly for injection of one or more cryogenic fluids from a hose, for example. Any apparatus or set-up for applying cryogenic temperatures to the metal test samples is envisioned and could be configured by one of ordinary skill in the art.

In the embodiments of FIGS. 1A and 1B, another rod 25 with threaded ends secures to lower female connector 35 and extends downward into threaded engagement with another upper female connector 23. The upper threaded end 19 of the lower test specimen 13 secures to another upper female connector 23. Another cup assembly 31 mounts to the lower test specimen 13 in the same manner as the upper cup assembly 31. Another lower female connector 35 secures to the lower threaded end of the lower test specimen 13, squeezing bottom 32 of cup assembly 31 between it and the nut 29 located in the lower cup assembly 31. Lower connector 35 is secured in various manners to a fixed point, such as a rigid test frame, to enable the tensile force F to pass through both test specimens 13. In other embodiments, metal test specimens can be secured and gripped at their ends with other configurations in lieu of threaded connections, such as for example with button-head connections.

Once assembled, a selected load or tensile force F, for example about 5,000 pounds to about 15,000 pounds will be applied to test assembly 11 while at room temperature, but greater or lesser forces may be chosen depending on the selected geometry of the test sample. The load is a fraction, such as 75%, of the theoretical notched tensile strength of test specimens 13, assuming that test specimens 13 do not have excessive or damaging levels of hydrogen therein. Excessive or damaging levels of hydrogen can vary depending on the type of metal sample to be tested, such as a steel alloy, its heat treat level, and/or special processing features. This load will be sustained for a selected time empirically determined sufficient to incubate and grow potential nascent hydrogen embrittlement micro-cracks. Embodiments of the present disclosure apply a constant strain rate during hydrogen embrittlement testing.

Micro-cracks will incubate only if sufficient hydrogen is located in the test specimens 13 at dangerous levels. Sufficient hydrogen to cause micro-cracks at a given temperature will depend upon the metal sample being tested, the temperature at which tension is applied, and the amount of tension/force applied to a sample. These parameters will vary based upon the strength and durability required of a given metal in a given application, for example aircraft.

At room temperature, the selected time may be about 20 hours. During the initial micro-crack incubation phase, stress induced migration and linkup of hydrogen atoms occurs at areas of atomic instability, i.e. stacking faults, dislocation slip planes, etc. The atomic hydrogen can act by itself or by re-combination into molecular hydrogen. At this point, micro-cracking begins. During a growth stage, the incubated micro-cracks continue to grow, enlarging in size, but will remain at a sub-critical size, below a critical flaw size that can cause a complete fracture or parting of test specimens 13 at room temperature.

In prior art room temperature hydrogen embrittlement testing, incubated micro-cracks may grow until they reach a critical flaw size, at which time the particular test specimen under tensile load would fracture. In prior art room temperature tensile testing for hydrogen embrittlement, the test specimen is considered free of any micro-cracks with a critical flaw size if a fracture has not occurred after 200 hours of sustained tensile load. If fracturing did occur during the 200 hour time period at room temperature, the micro-cracks would have grown, linked up, and eventually exceeded a critical flaw size.

In embodiments of the present disclosure, the sustained load at room temperature is applied for a much lesser period of time, for example about 20 hours, or about ¹/₁₀ the time required in certain prior art testing. Other shorter or longer incubation periods may be chosen with temperatures greater or lesser than room temperature. About 20 hours has been found to be sufficient to incubate micro-cracking if dangerous levels of hydrogen exist in test specimens 13. It is not considered sufficient time for the micro-cracks to reach a critical flaw size at room temperature, however, to cause a fracture of the test specimen.

In this disclosure, at the end of an example 20 hour period, technicians apply a cryogenic fluid to test specimens 13, for example pouring a cryogenic liquid such as liquid nitrogen 45 into and through open upper end 33 of each cup assembly 31, while sustaining the tensile force F. The liquid nitrogen 45, which is at approximately −320 degrees F., will begin boiling off as it rapidly cools the entire test specimen 13. The technician will continue to top off liquid nitrogen 45 to each cup assembly 31 until the rapid boiling diminishes greatly. When test specimens 13 reach about −320 degrees F., mild to no boil off will occur, and the technicians can look down into each cup assembly 31 and see clear liquid nitrogen. This procedure takes only about 60 seconds. At this point, the test specimens 13 are under tensile force F at the cryogenic temperature of about −320 degrees F.

If neither test specimen 13 fractures within a few seconds, usually no more than about 20 seconds to a few minutes, after reaching the cryogenic temperature, the test specimens 13 will be considered to have passed the hydrogen embrittlement test. That is, if fracturing did not occur, there were no sub-critical micro-cracks incubated during the non-cryogenic portion of the test (for example tension at about 20 hours at about room temperature) that were large enough to have a critical flaw size when exposed to the cryogenic temperature brought about by the liquid nitrogen (or other cryogenic fluid). In other words, the testing personnel can assume that if the test specimens 13 had been left at room temperature for 200 hours, they would not have fractured and failed, and therefore the test specimens 13 do not have a dangerous or excessive level of hydrogen.

Incubated micro-cracks, if any, created while the test specimens 13 were at non-cryogenic temperature, such as for example room temperature, if large enough, will rapidly propagate catastrophically at the cryogenic temperature. The very cold temperature causes the predictable fracture toughness and the critical flaw size to decrease. The Peierls stress increases rapidly with cryogenic exposure, exhibiting a sharp rise in the critical yield strength, simultaneously diminishing the structure's ability to blunt any crack tips while under stress. Because the reduction in temperature greatly reduces the critical flaw size, hydrogen embrittlement can be detected far sooner than time required at room temperature for sub-critical micro-cracks to grow into critical flaw size.

As an alternative, rather than room temperature, the initial incubation period under a sustained load could be made at a slightly elevated temperature, for example at about 125 degrees F., and at a higher load, such as 85% of the theoretical tensile strength of the test specimens without hydrogen embrittlement. The incubation time is reduced further as the additional temperature and slightly higher load gently accelerate the diffusion of hydrogen, accelerating the incubation time for micro-cracks of sub critical flaw size to occur. Preservation of any existing hydrogen in a metal test sample during this elevated warming (EW) can be ensured by use of a castable metallic masking (CMM) surrounding all of or a portion of the test sample. CMM materials are very low melting temperature metals, for example certain alloys with lead and tin, and exhibit good diffusion barrier properties, for example against hydrogen diffusion, while at the same time exhibiting melt casting temperatures that do not influence the hydrogen embrittlement testing.

Empirical tests have been performed correlating time to failure for identically prepared test specimens at room temperature sustained load for up to 200 hours versus those tested in accordance with embodiments of this disclosure.

The test methods and systems of this disclosure have many advantages. Embodiments apply standard test specimen configuration, type, and manufacturing methods. The systems and methods do not require special load frame equipment. In addition, liquid nitrogen is not flammable, chemically reactive, or dangerous. Handling of liquid nitrogen is safe, easy, and straightforward. Methods and systems described here do not require extra dedicated consumable supplied or electronic metering/monitoring equipment.

Furthermore, the embodiments of systems and methods of the present disclosure operate under generally atmospheric pressure, and no pressurized hydrogen gas or pressurized liquid nitrogen is necessary or applied. In other words, the systems and methods operate in the absence of increased or reduced pressures, and in the absence of any externally applied hydrogen gas. Metal samples of the present disclosure are tested for pre-existing hydrogen embrittlement, or in other words hydrogen embrittlement that may occur during metal production, treatment, and/or finishing, and therefore hydrogen infusion to the metal samples for testing is not desired or required.

Embodiments of the invention described herein, therefore, are well adapted to carry out the objects and attain the ends and advantages mentioned, as well as others inherent therein. While presently preferred embodiments of the invention have been given for purposes of the disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. A method for testing for hydrogen embrittlement, the method comprising the steps of:
    applying a tensile load to a metal test specimen comprising a notched area and sustaining the load for a selected duration to incubate potential hydrogen embrittlement cracks with a sub-critical flaw size if sufficient hydrogen is present in the test specimen;
    then, while sustaining the load, immersing and chilling the notched area with a cryogenic fluid reducing the sub-critical flaw size for any hydrogen embrittlement cracks incubated; and
    with the sustained load, fracturing the notched area if the sub-critical flaw size of any hydrogen embrittlement cracks incubated reaches a critical flaw size, wherein the selected duration is determined by comparing an amount of time it takes to fracture at or above room temperature test specimens having known hydrogen at dangerous levels versus an amount of time it takes to fracture identically prepared test specimens having known hydrogen at dangerous levels when chilled with the cryogenic fluid.

2. The method according to claim 1, wherein the step of immersing and chilling the notched area with a cryogenic fluid is carried out using a cryogenic assembly disposed around the metal test specimen.

3. The method according to claim 2, wherein the cryogenic assembly comprises a container having a closed bottom below the notched area on the test specimen and an open upper end above the notched area.

4. The method according to claim 1, wherein:
    the step of immersing and chilling the notched area includes dispensing a cryogenic fluid comprising liquid nitrogen and comprises continuing to dispense the cryogenic fluid until rapid boiling of the cryogenic fluid ceases around the metal test specimen.

5. The method according to claim 1, wherein:
    the step of immersing and chilling the notched area comprises continuing to dispense the cryogenic fluid until the notched area reaches a temperature of the cryogenic fluid.

6. The method according to claim 1, wherein fracturing of the notched area occurs within a few seconds to a few minutes after chilling the notched area in test specimens having known hydrogen at dangerous levels.

7. The method according to claim 1, wherein:
    the step of applying the tensile load for a selected duration occurs while the test specimen is at room temperature.

8. The method according to claim 1, wherein:
    the step of applying the tensile load for a selected duration comprises the step of applying the tensile load for an elevated temperature duration at an elevated temperature above room temperature,
    wherein the elevated temperature duration is less than the selected duration while at room temperature.

9. The method according to claim 8, further comprising the step of applying a castable metallic masking to at least a portion of the metal test specimen.

10. The method according to claim 1, wherein the cryogenic fluid comprises a cryogenic fluid other than liquid nitrogen.

11. A system for testing for hydrogen embrittlement, the system comprising:
    a securing mechanism for securing a metal sample;
    a tension applying mechanism for applying tension to the metal sample once secured by the securing mechanism; and
    a cryogenic assembly for applying a cryogenic fluid to the metal sample under atmospheric pressure to test for hydrogen embrittlement of the metal sample while the metal sample is under tension, wherein securing the metal sample for testing creates a cryogenic seal with the cryogenic assembly, the metal sample forming a part of the cryogenic seal.

12. The system according to claim 11, wherein the cryogenic fluid comprises liquid nitrogen, and the tension applied to the metal sample is between about 5,000 to about 15,000 pounds-force.

13. The system according to claim 11, wherein the cryogenic assembly comprises an open-top cup assembly operable to allow for pouring of liquid nitrogen to surround the metal sample while the metal sample is under tension.

14. The system according to claim 11, wherein the securing mechanism and tension applying mechanism comprise threads.

15. The system according to claim 11 further comprising a heating mechanism operable to heat the metal sample during tension and prior to applying the cryogenic fluid.

16. The system according to claim 11 further comprising a sealing mechanism between the tension applying mechanism, the cryogenic assembly, and the metal sample operable to prevent leakage of the cryogenic fluid from the cryogenic assembly.

17. The system according to claim 11, wherein the system is operable to test more than one metal sample simultaneously for hydrogen embrittlement.

18. The system according to claim 11, further comprising a temperature measuring mechanism to detect when the temperature of the metal sample is at about the temperature of the cryogenic fluid.

19. The system according to claim 11, wherein the securing mechanism comprises two female connectors to secure the metal sample on opposite ends of the metal sample, wherein each female connector has at least a portion of the connector disposed external to the cryogenic assembly when the sample is secured.

* * * * *